United States Patent [19]

Kaufman

[11] 4,340,068
[45] Jul. 20, 1982

[54] MULTIPLE SAMPLE NEEDLE WITH VEIN ENTRY INDICATOR

[75] Inventor: Joseph Kaufman, Emerson, N.J.

[73] Assignee: Becton, Dickinson and Company, Paramus, N.J.

[21] Appl. No.: 160,781

[22] Filed: Jun. 18, 1980

[51] Int. Cl.$^3$ ............................................. A61B 5/14
[52] U.S. Cl. ............................. 128/766; 128/218 NV
[58] Field of Search ............... 128/766, 218 NV, 215, 128/216, 760, 763, 764

[56] References Cited

U.S. PATENT DOCUMENTS

| | | | |
|---|---|---|---|
| 4,106,497 | 8/1978 | Percarpio | 128/766 |
| 4,207,870 | 6/1980 | Eldridge | 128/766 |
| 4,244,379 | 1/1981 | Smith | 128/766 |

*Primary Examiner*—John D. Yasko
*Attorney, Agent, or Firm*—Richard J. Rodrick

[57] ABSTRACT

A multiple sample needle assembly for determining fluid access when collecting fluid samples from a source of fluid into a vacuum collection device. The assembly includes a housing with a chamber therein having first and second access openings in fluid communication with the chamber. The housing is preferably translucent to provide for the viewing of the contents of the chamber. A cannula is associated with the first access opening, while the second access opening is adapted for fluid communication with the vacuum collection device. An operable, resilient valve member is positioned in the chamber and is normally closed against a gas permeable, liquid impermeable plug member mounted in the valve member. This valve member is adapted to open away from the plug member when the pressure at the second access opening is less than the pressure at the first access opening. When the cannula makes entry into the fluid source, fluid enters the chamber by forcing any gas therein through the porous plug member with the fluid in the chamber being viewable by the user. This fluid is adapted to remain in the chamber until the valve member opens under the pressure differential.

11 Claims, 6 Drawing Figures

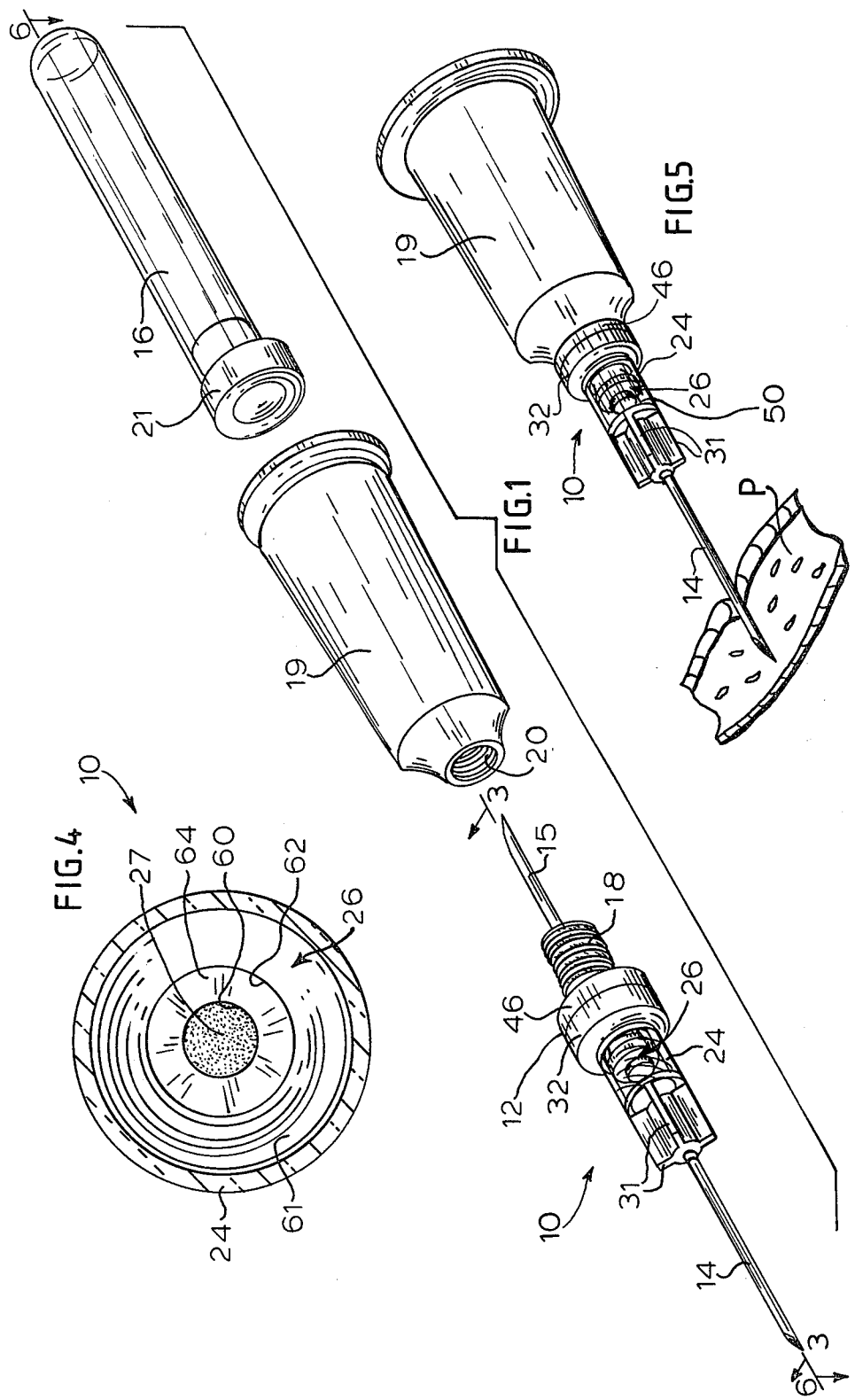

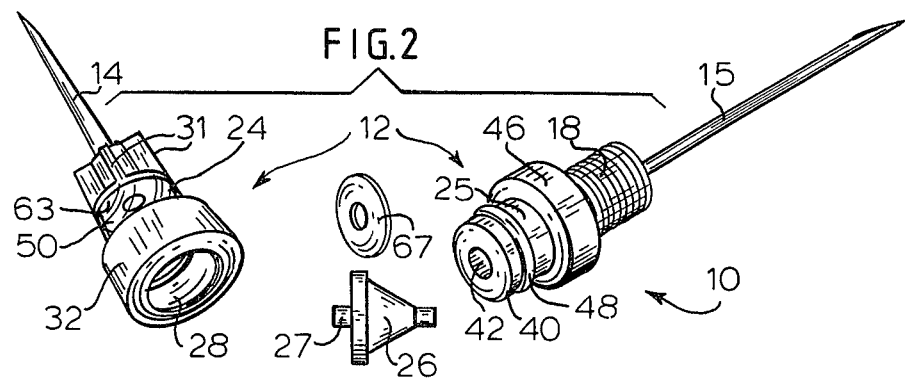
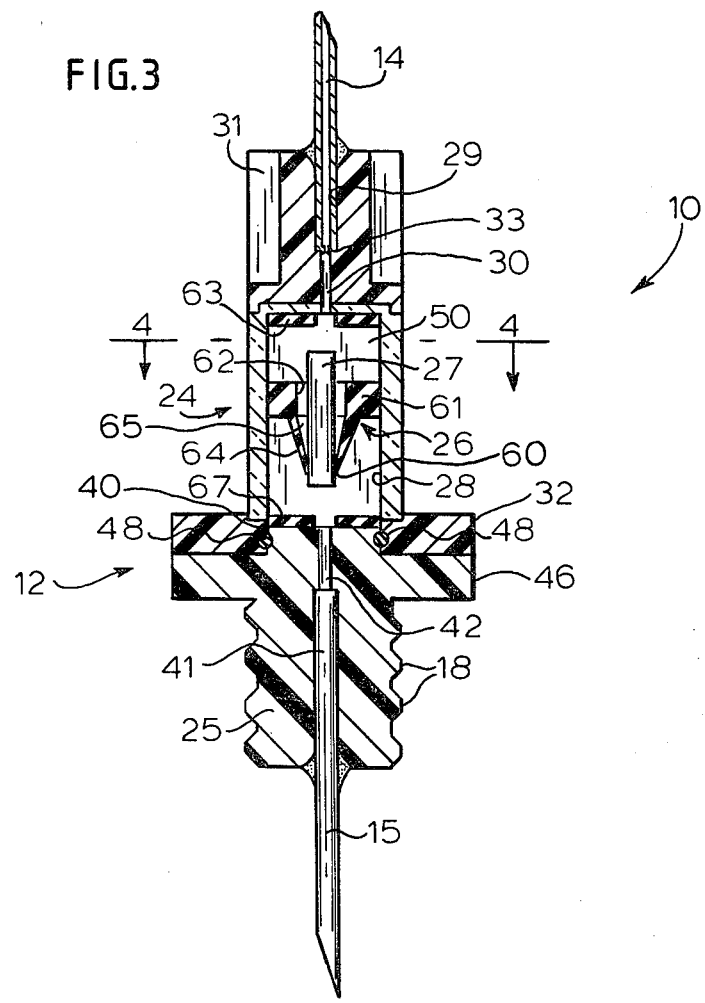

MULTIPLE SAMPLE NEEDLE WITH VEIN ENTRY INDICATOR

BACKGROUND OF THE INVENTION

The present invention relates to a needle assembly for collecting fluid such as from a patient, and more particularly, concerns a needle assembly for collecting multiple samples of fluid from a patient with an anti-backflow valve included in the assembly with a provision for indicating the entry of the needle assembly into the vein of the patient.

In the collection of fluids, and especially when such fluids may be blood or other bodily fluids from a patient, it is most desirable that backflow into the patient or other source be prevented. The reasons for prevention of fluid backflow into the patient are numerous. For example, when collecting blood into a collection container, various chemicals or other reagents may be present in the container for different tests on the blood sample. As the blood sample flows into this container, it mixes with the chemical therein. Should this mixture backflow into the patient, the chemical would then enter into the patient's blood stream with potential harm. Another instance where backflow into the patient could be problematical involves clotting of the blood during the collection procedure. Should a small amount of the collected blood clot somewhere in the collection needle or container, backflow of such a clotted or coagulated amount of blood into the patient could cause serious difficulties. Accordingly, the inclusion of some type of anti-backflow device or valve into a needle assembly for the collection of fluids from a patient is a desired feature.

In addition, it is also desirable to provide a mechanism whereby the user of such a needle assembly can be informed when the intravenous needle has penetrated the vein of the patient. Many times in collecting blood from a patient it is difficult to locate the vein or for other reasons blood flow into the collection device is minimal. In these instances, it becomes most advantageous to be able to make a quick determination that entry into the vein has been made and that blood is flowing into the needle assembly. Once this determination has been made and vein entry indeed accomplished, the evacuated blood collection container can then be inserted into the collection assembly in accordance with these well known techniques of collecting multiple blood samples during a single collection procedure.

One of the problems which arises during the venipuncture step concerns the pocket of air which is found in various needle assemblies useful for multiple sample blood collections. When venipuncture is made, and the evacuated blood collection container is not yet attached to the opposite end of the needle structure, blood cannot always flow into the needle assembly because of this pocket of air which, under normal atmospheric conditions, remains inside the needle assembly. Accordingly, even though vein entry may have been accomplished, the blood may not move through the intravenous needle into the collection assembly under tourniquet pressure until the evacuated blood collection container is attached, whereupon the vacuum source causes sufficient draw through the needle assembly. In a previously filed patent application entitled "Blood Sampling Assembly Having Vein Entry Indicator" by William N. Eldridge, U.S. Ser. No. 915,670, filed June 15, 1978, and assigned to the common assignee herewith, the inventor recognized that this air blockage problem prevented the blood from flowing through the intravenous needle to a point where it could be seen by a user. In the Eldridge invention, a porous vent means is provided in conjunction with a one-way valve whereby air inside the needle assembly is allowed to pass out of this venting means during the initial stages of the blood collection procedure. However, the venting means prevents the passage of blood for at least a reasonable amount of time, such as may be long enough for the user to attach the evacuated blood collection container to the needle assembly. Once the negative pressure of the evacuated blood collection container is attached, the one-way valve opens up and allows blood to travel from the vein of the patient, through the needle assembly and on into the container.

Although the Eldridge invention is most advantageous in providing the combination one-way valve and air venting means, there is still room for improvement thereover. The present invention is directed to improving the type of combination in a needle assembly suggested by Eldridge.

SUMMARY OF THE INVENTION

A multiple sample needle assembly for determining fluid access when collecting fluid samples from a source of fluid into a vacuum collection device comprises a housing with a chamber therein, having first and second access means in fluid communication with the chamber. Means for viewing the contents of the chamber is provided in the housing. A cannula for insertion into the fluid source extends from the first access means in fluid communication with the chamber, whereas the second access means is adapted for fluid communication with a vacuum collection device. Operable, resilient valve means is positioned in the chamber normally closed against a gas permeable, liquid impermeable plug member mounted in the valve means. The valve means is adapted to open away from the plug member when the pressure at the second access means is less than the pressure at the first access means. When the cannula makes entry into the fluid source, fluid enters the chamber by forcing any gas therein through the porous plug member. Fluid in the chamber is then able to be viewed by the user through the viewing means. This fluid is adapted to remain in the chamber at least for a reasonable period of time, until the valve means opens under the pressure differential.

In a preferred embodiment of the needle assembly of the present invention as generally set forth above, the housing has a forward end and a rearward end with the chamber within. A first cannula extends from the first access opening and is adapted for insertion into a patient. Extending from the second access opening in the rearward end of the housing is a second cannula which is adapted for penetration of an evacuated container for collection of a blood sample. The valve means preferably includes a resilient, operable element which is adapted to open and close depending upon the pressure differential thereacross. The porous plug is preferably mounted so that it is positioned inside the operable element so that the element can close against and open away from the plug. In use, when the cannula makes entry into the vein of the patient, blood can enter into the chamber and dispel any air therein through the porous plug thereby allowing the blood to enter the chamber without any air blockage. The liquid impermeability feature of the plug will prevent the blood from passing therethrough inasmuch as the valve will still be in the normally closed position. The user can then view the blood inside the chamber through a portion of the housing which is preferably translucent. At this time, the user can then attach, in the known fashion, an evacuated blood collection container to the needle assembly. When this is accomplished, the pressure at the second access opening inside the needle assembly is at a lower pressure than the pressure at the first access opening in the needle assembly on the other side of the one-way valve. This pressure differential is sufficient to open the operable valve element thereby allowing the blood to flow through the needle assembly and on into the blood collection container.

In accordance with the principles of the present invention, there are structural elements and features herein which are notably different from prior inventions of this type, notably the Eldridge invention. In Eldridge's invention, the one-way valve opens and closes against the wall surrounding the chamber. Effective contact must be made by the operable valve element of Eldridge in order to assure that blood does not leak around the element if there are any leaks. In order to minimize any leakage problem which could be formed in Eldridge's invention, the present invention provides for the valve element to contact the porous plug rather than the wall surrounding the chamber. In this fashion, the surface area of contact is substantially diminished so that any leakage problems can also be minimized. Furthermore, the present invention may employ in an embodiment thereof a conically shaped valve which is adapted to normally open and close under a given set of pressure conditions on respective sides of the valve. Therefore, it can be seen that the present invention may utilize relatively inexpensive, easily accessible components in order to be effective. As a result, the present invention provides both anti-backflow and vein entry indication features in an improved structural relationship over the prior art.

BRIEF DESCRIPTION OF THE DRAWINGS

FIG. 1 is an exploded perspective view illustrating the preferred multiple sample needle assembly, a holder for an evacuated container and an evacuated blood collection container for use in obtaining blood samples from a patient;

FIG. 2 is an exploded perspective view illustrating the components of the preferred multiple sample needle assembly of the present invention;

FIG. 3 is an enlarged cross-sectional view taken along line 3—3 of FIG. 1;

FIG. 4 is an enlarged end view of the valve member and porous plug looking along line 4—4 of FIG. 3;

FIG. 5 is a perspective view of the needle assembly connected to a holder inserted into a patient so that a user can view same for indication of vein entry.

DETAILED DESCRIPTION

Figure 6:
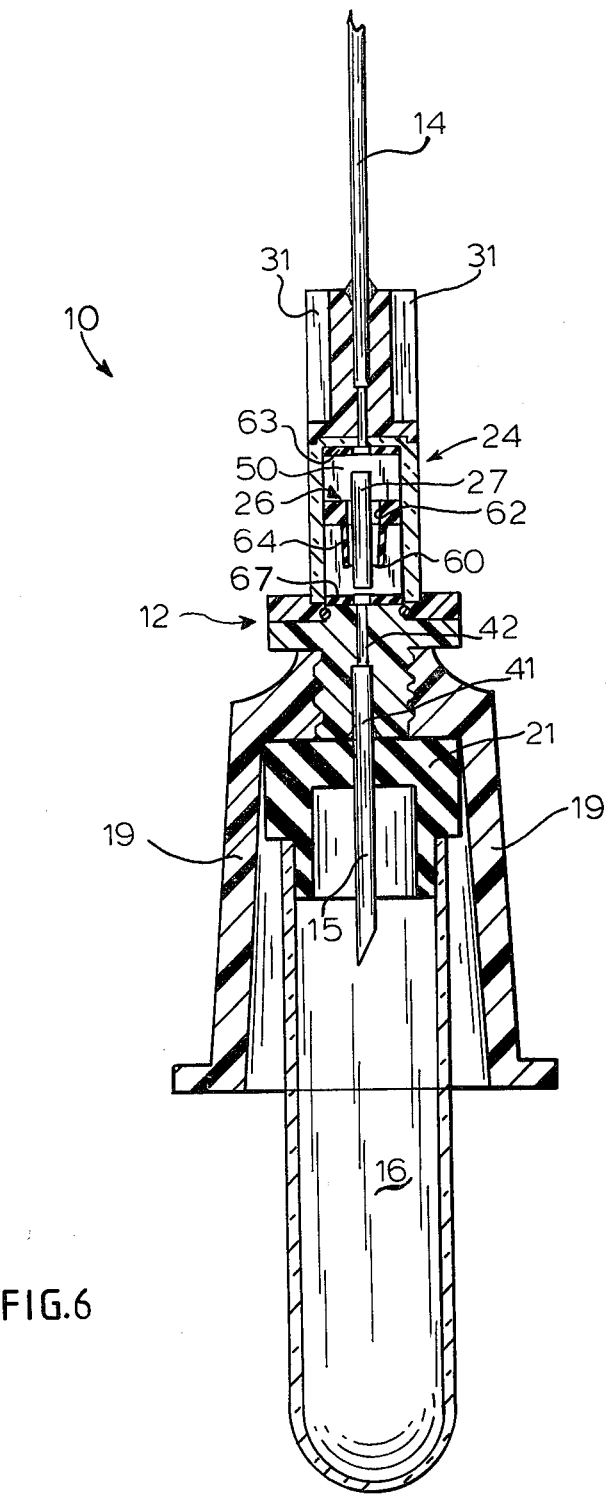
FIG. 6 is a cross-sectional view taken along line 6—6 of FIG. 1 with the components in an assembled condition as they would appear during use.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims.

Referring to the drawings, particularly to FIG. 1, there is illustrated the preferred embodiment of a multiple sample needle assembly 10. The basic external components of needle assembly 10 include a housing 12, a first needle cannula 14 adapted for insertion into a patient and a second needle cannula 15 at the opposite end of housing 12, the second needle cannula adapted for penetration of an evacuated container 16 for collection of a blood sample. Housing 12 includes a threaded portion 18 adjacent second cannula 15 onto which a container holder 19 is threaded by its internal mating threads 20 at the forward end of the holder. Evacuated container 16 slides into holder 19 so that second needle cannula 15 can penetrate the penetrable stopper 21 at the forward end of the evacuated container. These general aspects of multiple sample blood collections in this type of structure are well known to those skilled in this art.

In FIGS. 2, 3 and 4, the detailed construction of needle assembly 10 is illustrated. Housing 12 has a forward end 24 and a rearward end 25, these ends being preferably separable in order to place valve member 26 and porous plug 27 in their proper positions. Forward end 24 is preferably cylindrically shaped and has a large bore 28 extending into and partially through its body. At the other end of this section a smaller bore 29 is included which is generally sized to slidably fit needle cannula 14 therein. In this embodiment being described, smaller bore 29 does not extend completely through forward end 24 to communicate with larger bore 28. However, a still smaller diameter channel 30 interconnects these two bores so that there is fluid communication from needle cannula 14 into larger bore 28. At the junction between bore 29 and channel 30 a shoulder 33 is formed. Needle cannula 14 abuts against this shoulder 33 for proper positioning. Once the needle cannula is in position it can be suitably affixed such as by adhesive means or the like. It is appreciated that the presence of channel 30 is not essential to the structure of this forward end of the housing, but is merely a preferable element. However, it will be appreciated that the diameter of channel 30 can be varied to provide a regulation of the fluid flow rate which flows therethrough.

Forward end 24 of the housing also includes a number of longitudinal ribs 31 surrounding the outwardly extending cannula. A needle shield (not shown) generally covers the outwardly extending needle cannula and includes mating internal ribs within. The mating ribs between needle shield and needle assembly allow the user to facilitate the insertion or removal of the needle assembly into the tube holder. Forward end 24 also includes an annular flange 32 which serves to provide a surface for joining the two portions of the housing together upon assembly. Once again, suitable fastening means, such as adhesives or the like may be used to secure the two portions of the housing together.

Rearward end 25 includes a short protruding portion 40, generally cylindrically shaped, and sized to fit within larger bore 28 of the forward end. At the opposite side of this rearward end, external threads 18 are provided as previously mentioned as a connection mechanism to the tube holder. A bore 41 extends partially through the rearward end of the housing which is substantially similar to bore 29 in the forward end of the housing. Once again, bore 41 is sized to accept the diameter of second needle cannula 15, which is secured to bore 41 by appropriate means, including adhesives and the like. A smaller diameter channel 42 communicates with bore 41. An annular flange 46 is provided to cooperate with flange 32 in joining the two ends of the housing together. To assure proper fluid flow through the housing, an annular, elastomeric ring 48 may be included in this embodiment around protruding portion 40. Upon assembling forward end and rearward end together, with valve member 26 and porous plug 27 placed in their proper positions, respective flanges 32 and 46 are secured together by appropriate fastening means, such as adhesives and the like. Protruding portion 40 within larger bore 28 leaves an internal space around the valve member and porous plug forming a chamber 50 within the housing.

In order to be able to visualize the contents of chamber 50, it is preferred that at least a portion of housing 12, such as in the forward end, be translucent or transparent. For ease of manufacture, it is most desirable to make the entire forward end of the needle assembly from such a translucent material such as translucent rigid plastic and the like. Various sealed windows, ports or other means for a user to view the contents of the chamber are within the purview of this invention; it is preferable that such window or port be sealed so that any blood which enters chamber 50 upon the needle entering the vein will not escape from this assembly.

Valve member 26 is preferably conically shaped with a rounded cross-section, and is positioned within chamber 50 so that it extends transversely across. In order to fix valve member 26 in place, its outside diameter around its wide base portion 61 is sized for an interference fit against the walls of bore 28. Valve member 26 includes a substantially centrally located hole 60 at its narrow end and a wider opening 62 at the base portion of the valve. The operable valve element of this valve is a resilient, substantially conically shaped extension 64 defining a hollow cavity 65 within. There is fluid communication between opening 60 at the narrow end of the valve, cavity 65 and wider opening 62 whereby fluid can flow through the valve member when in an open position.

Porous plug 27, preferably a cylindrically shaped element, is a gas permeable, liquid impermeable element adapted to let gas, such as air pass through but not liquid, such as blood, pass through. This plug is sized so as to fit within hole 60 in the valve member when conical extension 64 is in the relaxed condition. The plug is oriented so that it extends through cavity 65 and through opening 60 at the narrow end of the extension element. In this fashion, and due to the resiliency of the valve member, the extension element is adapted to close against porous plug 27 in a fluid-tight sealing engagement, such as would be produced by an interference fit between these components. A closed valve is thus formed, which is normally closed under atmospheric pressure conditions, such as when the pressures on opposite sides of the valve are substantially equal.

Before turning to the use of the present invention, the valve member of this invention and the operable valve element are preferably integrally formed as a unitary element. Elastomeric materials are best suited for the valve member and operable element, with sufficient resiliency to provide the necessary fluid-tight sealing engagement between valve member and porous plug. While the porous plug may be made of many materials, it is preferred that it be fabricated of sintered polyethylene.

Turning now to FIG. 5, the preferred needle assembly 10 is illustrated connected to a multiple sample holder 19. Cannula 14 is shown inserted into a patient P during the venipuncture procedure. Valve member 26 (not shown in FIG. 5) is designed so that it will remain closed under normal tourniquet pressure. With the inclusion of porous plug 27 cooperating to keep valve member 26 closed, the pressure inside the patient's vein will force blood through cannula 14 into forward end 24 of the housing and then into chamber 50. Any air which may be initially inside chamber 50 will then be forced out by the entering blood through porous plug 27, which is air permeable, but blood impermeable. With at least forward end 24, or a portion thereof, being translucent, the user of this needle assembly can then view the blood as it enters chamber 50 and remains there for a reasonable time span. As soon as the user sees the blood in chamber 50, it serves as an indication that vein entry has been made. Conversely, if the user does not see blood flow into chamber 50, it can safely be assumed that vein entry has not been accomplished. With this feature, the user does not have to attach an evacuated blood collection container until vein entry indication has been determined. The porous plug of the present invention is sufficient to retain the collected blood inside the chamber at least for a period sufficiently long to allow an evacuated blood collection container to be inserted into collection holder 19.

FIG. 6 illustrates the evacuated blood collection container 16 inserted into holder 19 so that penetrable stopper 21 is penetrated by hollow cannula 15. Once second cannula 15 is into the vacuum area inside container 16, the pressure at the opening of channel 42, in fluid communication now with the vacuum inside container 16, becomes negative with respect to the pressure at channel opening 30 on the opposite side of valve member 26. Allowing for any residual resistive forces in the resilient valve member material, this negative pressure causes extension 64 to open and operatively move away from and break its sealing engagement with porous plug 27. At this time, needle cannula 14 has already been inserted into the vein of the patient so that blood has been collected in chamber 50 on the other side of the valve. Once the operable extension 64 is open, blood may now flow through cannula 14, chamber 50 and through wide opening 62 and on past the open resilient extension 64. From there, blood flows into channel 42, second cannula 15 and on into collection container 16. It should be pointed out that when extension 64 is not contacting plug 27 and the valve is therefore open, the plug is somewhat free-floating in the axial direction. To prevent the floating plug from blocking channels 30 and 42 at respective ends of the chamber, axial stops 63 and 67 are provided. These stops may be ribs, protrusions or the like to keep the plug from blocking the channels, but still allowing blood flow through the chamber.

If backflow of any blood or other fluids should occur, valve member 26 and particularly operable extension 64, is adapted to resiliently spring back against the porous plug to thereby close off fluid flow. When the user of this composite assembly has collected enough blood into container 16, the filled container is withdrawn thereby terminating the vacuum conditions at cannula 15. Operable resilient extension 64, perceiving this change of pressure, springs back to close off further fluid flow by seating against the porous plug. It should be pointed out that the spring force of the resilient operable valve element should be sufficient to provide a closed valve even while needle cannula 14 remains inserted into the vein of the patient.

Thus, the multiple sample needle assembly of the present invention includes an anti-backflow valve which is easily mounted in the assembly inexpensive to produce and functional in its operation. In addition, this needle assembly includes a mechanism for indicating vein entry to the user of this invention. Both of the aforementioned features contribute to the efficient use of this type of assembly in the multiple sample collection procedure.

What is claimed is:

1. A multiple sample needle assembly for determining vein entry when collecting blood samples from a patient into an evacuated container comprising:
   a housing having a forward end, rearward end and a chamber within, said housing being translucent at least around the chamber so that said chamber can be viewed by a user of said assembly;
   a first access opening through the forward end of said housing in fluid communication with said chamber;
   a cannula extending outwardly from said first access opening in fluid communication with said chamber adapted for insertion into a patient;
   a second access opening through the rearward end of said housing in fluid communication with said chamber;
   an operable, resilient, normally closed one-way valve member positioned in said chamber including an operable element adapted to open and close depending upon the pressure differential across said operable element; and
   an air permeable, blood impermeable porous plug mounted in said valve member and associated with said operable element so that said element closes against said plug and operatively opens by moving away from said plug, whereby when said cannula makes entry into the vein of a patient blood enters said chamber by forcing air therein through said porous plug, the blood in said chamber able to be viewed by the user through said translucent housing, with the blood adapted to remain in said chamber until said valve member opens under the influence of lower pressure at said second access opening.

2. The assembly of claim 1 wherein said operable element of said valve member is a substantially conically shaped, resilient extension defining a hollow cavity within with a blood flow opening at its distal end and oriented in said chamber so that said distal end faces toward said second access opening.

3. The assembly of claim 2 wherein said porous plug extends through said hollow cavity and said blood flow opening, with said resilient extension being normally closed against said porous plug to provide a blood-tight seal.

4. The assembly of claim 1 wherein said valve member and said operable element are integrally formed as a unitary element.

5. The assembly of claim 1 wherein said valve member and said operable element are made of an elastomeric material.

6. The assembly of claim 1 wherein said porous plug is made of sintered polyethylene.

7. The assembly of claim 1 wherein a second cannula extends from said second opening in fluid communication with said chamber adapted for penetration of an evacuated container for collection of a blood sample.

8. The assembly of claim 1 wherein the housing includes means for connecting a holder for an evacuated container.

9. The assembly of claim 8 which further includes a holder for an evacuated container connected to said housing.

10. A multiple sample needle assembly for determining fluid access when collecting fluid samples from a source of fluid into a vacuum collection device comprising:
    a housing with a chamber therein and having first and second access means therethrough in fluid communication with said chamber, said housing including means for viewing the contents of the chamber therein, said second access means adapted for fluid communication with said vacuum collection device;
    a cannula for insertion into said fluid source extending from said first access means in fluid communication with said chamber; and
    operable, resilient valve means positioned in said chamber normally closed against a gas permeable, liquid impermeable plug member mounted in said valve means, said valve means adapted to open away from said plug member when the pressure at said second access means is less than the pressure at said first access means, whereby when said cannula makes entry into said fluid source, fluid enters said chamber by forcing any gas therein through said porous plug member, the fluid in said chamber able to be viewed by the user through said viewing means, with the fluid adapted to remain in said chamber until said valve means opens under said pressure differential.

11. A multiple sample needle assembly for determining vein entry when collecting blood samples from a patient into an evacuated container comprising:
    a housing having a forward end, a rearward end and a chamber within, said housing being translucent at least around the chamber so that said chamber can be viewed by a user of said assembly;
    a first access opening through the forward end of said housing in fluid communication with said chamber;
    a first cannula extending from said first access opening in fluid communication with said chamber and being adapted for insertion into a patient;
    a second access opening through the rearward end of said housing in fluid communication with said chamber, said first and said second openings being in substantial alignment on opposite sides of said chamber;
    a second cannula extending from said second access opening in fluid communication with said chamber and being adapted for penetration of an evacuated container for collection of a blood sample;
    an operable, resilient, elastomeric normally closed one-way valve member positioned in said chamber, including an operable substantially conically shaped extension defining a hollow cavity within with a blood flow opening at its distal end and oriented in said chamber so that said distal end faces toward said second access opening, said operable extension adapted to open and close depending upon the pressure differential across said valve; and
    an air permeable, blood impermeable porous plug mounted in said valve member so that said plug extends through said hollow cavity and said blood flow opening with said resilient extension being normally closed against said porous plug to provide a blood-tight seal, said resilient extension adapted to operatively open by moving away from said plug, whereby when said first cannula makes entry into the vein of a patient, blood enters said chamber by forcing air therein through said porous plug, the blood in said chamber able to be viewed by the user through said translucent housing, with the blood adapted to remain in said chamber until said valve member opens under the influence of lower pressure at said second access opening.

* * * * *